United States Patent [19]

Kim et al.

[11] 4,040,785
[45] Aug. 9, 1977

[54] LYSABLE BLOOD PRESERVATIVE COMPOSITION

[75] Inventors: Young Ran Kim, Hartsdale; Leonard Ornstein, White Plains, both of N.Y.; Henry Cook Waters, III, Oxford, Conn.

[73] Assignee: Technicon Instruments Corporation, Tarrytown, N.Y.

[21] Appl. No.: 733,435

[22] Filed: Oct. 18, 1976

[51] Int. Cl.² .......................................... G01N 33/16
[52] U.S. Cl. ................................. 23/230 B; 195/1.8
[58] Field of Search ..................... 195/1.8; 424/101; 23/230 B

[56] References Cited

U.S. PATENT DOCUMENTS

| | | | |
|---|---|---|---|
| 3,703,438 | 11/1972 | Dovgalev et al. | 195/1.8 |
| 3,847,738 | 11/1974 | Brake et al. | 195/1.8 |
| 3,859,049 | 1/1975 | Ware et al. | 23/230 B |
| 3,925,153 | 12/1975 | Laborit | 195/1.8 |

*Primary Examiner*—Sam Rosen
*Attorney, Agent, or Firm*—Morgan, Finnegan, Pine, Foley & Lee

[57] ABSTRACT

Blood is preserved by combining samples with a preservative reagent consisting of an aqueous mixture of a mono-, di- or trisaccharide component and formaldehyde.

13 Claims, No Drawings

LYSABLE BLOOD PRESERVATIVE COMPOSITION

BACKGROUND OF THE INVENTION

With the advent of hematologic automation by use of continuous flow systems, it became possible for technicians to substantially increase the number of samples which could be analyzed over a fixed period of time. However, concomitant with this vast improvement in efficiency, there arose the need for stabilizing or preserving whole blood samples in order to facilitate the logistics of specimen transportation from remote locations and the batching of specimens for presentation to automated hematologic systems.

SUMMARY OF THE INVENTION

It is the purpose of this invention to extend the life of blood specimens so that accurate white blood cell differential counts can be obtained on continuous flow automated systems for blood specimens more that 1 day old.

In accordance with that objective, the present invention is directed to a preserved lysable anticoagulated blood composition comprising a mixture of blood sample and preservative reagent wherein said preservative reagent comprises an aqueous mixture of a mono-, di- or trisaccharide component and formaldehyde, the resulting preserved blood composition containing said saccharide in the range of from 0.05% to 1.0% by weight and said formaldehyde in the range of from 0.1% to 0.8% by weight.

In a preferred embodiment, the preservative reagent consists of dextrose (a monosaccharide) and formaldehyde.

In one preferred embodiment, the resultihg preserved blood composition contains dextrose and formaldehyde in amounts of 1% by weight and 0.2% by weight respectively. In another preferred embodiment, the resulting preserved blood composition contains dextrose and formaldehyde in amounts of 0.66% by weight and 0.13% by weight respectively.

DETAILED DESCRIPTION OF THE INVENTION

In a continuous automated flow system apparatus such as Hemalog D[1] which is a screening laboratory instrument designed to ease the burden of differential white blood cell counting, cytochemical procedures specifically identify and label individual cell types. The stream of stained and unstained cells flows through an optical view chamber where a photoelectric measuring process takes place. Electronic signals are sorted by amplitude and classified into categories corresponding to the several cell types. Data are printedfor one sample/min. on the five major white cell types of whole blood, as well as juvenile forms of neutrophils and an unclassified remainder, in the form of percentage and cells/min.[3].

[1] This is a registered trademark of Technicon Instruments Corp.

In the preserved blood compositions of this invention, the red cells remain lysable. This is highly desirable since in most automated white blood cell counting systems, as in the Hemalog D, red cells must be lysed or they will interfere with the cell counting and indentification process.

The specific chemical-identifying process stains the white cells.

To ensure correct analyses on such systems, the blood sample must be essentially in the same state as when drawn from a patient. It is known that as blood ages, degradation occurs which could lead to an incorrect analysis. For instance, in the Hemalog D apparatus, since classification of cells are based on enzymatic activity, as the blood stands or ages, this activity is subject to change and therefore questionable results. Furthermore, blood specimens on standing are subjected to other undesirable occurrences, such as clumping and cell breaking.

Because these unwanted occurrences are apt to become more pronounced as the blood sample stands for any length of time, it has become necessary to find ways to preserve the basic nature of the sample for an extended period of time so that when analysis is effected, the results are dependable.

Accordingly, the present invention is directed to a preserved lysable anticoagulated blood composition whereby the analytic life of the blood specimen to be analyzed is extended to periods up to and beyond 72 hours at 4° C and up to and beyond 48 hours at 25° C. The advantages and benefits derived from such a preservative system are apparent — the technician need not be concerned with running the sample through the apparatus within 24 hours which could be a problem if a large number of samples are received.

The preserved lysable anticoagulated blood composition of this invention comprises a mixture of blood sample and a preservative reagent, the latter comprising an aqueous mixture of a mono-, di- or trisaccharide component, preferably a monosaccharide, and formaldehyde, all readily available materials.

Anticoagulent is supplied into the system by incorporation into the blood sample or the preservative reagent and in cases where a blood sample is drawn and thereafter immediately combined with preservative reagent, the latter embodiment is preferred. An illustrative useful anticoagulent for purposes of this invention is tripotassium ethylenediamine tetraacetic acid ($K_3EDTA$). In the final total blood composition, the concentration of $K_3EDTA$ is typically in the range from 0.1 to 0.2% by weight.

Illustrative monosaccharides for purposes of this invention include dextrose, fructose and galactose with dextrose being most preferred. Exemplary disaccharides include sucrose and maltose. An illustrative trisaccharide is raffinose.

The saccharide component and formaldehyde are combined in aqueous form using distilled or deionized water and preferably filtered, for instance, through a 0.8 $\mu$ filter.

After filtration, the reagent preservative is combined with a fresh whole blood sample.

The preserved lysable anticoagulated blood composition so formed is gently mixed, e.g. by inversion, and then stored at temperatures from 1° C to 25° C until ready for testing.

Such blood preserving compositions can be stored for periods beyond 24 hours and up to about 72 hours.

EXAMPLE I

A preserved lysable anticoagulated blood composition which can be stored at 4° C for at least 72 hours comprising a mixture of blood sample and preservative reagent, the latter consisting of an aqueous mixture of dextrose and formaldehyde wherein the resulting preserved blood composition contains dextrose and formaldehyde in amounts of 1% by weight and 0.2% by weight respectively is prepared as follows:

An aqueous mixture, in distilled or deionized form, containing 10% by weight dextrose and 2% by weight formaldehyde is filtered through an 0.8 μ filter and combined with an anticoagulated whole blood sample. The volume ratio of blood sample to reagent preservative is 10:1.

The resulting lysable preserved blood composition is gently mixed by inversion and stored at 4° C.

EXAMPLE II

Preserved lysable anticoagulated blood compositions similar to that described in Example I are prepared wherein in lieu of dextrose, the following saccharides are used:
monosaccharides: fructose, galactose
disaccharides: sucrose, maltose
trisaccharides: raffinose

EXAMPLE III

A preserved lysable anticoagulated blood composition which can be stored at 25° C for at least 48 hours comprising a mixture of blood sample and preservative reagent, the latter consisting of an aqueous mixture of dextrose, formaldehyde and tripotassium ethylenediamine tetraacetic acid ($K_3EDTA$) wherein the resulting preserved blood composition contains dextrose, formaldehyde and $K_3EDTA$ in amounts of 0.66% by weight, 0.13% by weight and 0.15% by weight respectively is prepared as follows:

An aqueous mixture, in distilled or deionized form, containing 20% by weight dextrose, 4% by weight formaldehyde and 4.5% by weight $K_3EDTA$ is filtered through an 0.8 μ filter and placed in a container under vacuum. A freshly drawn whole blood sample is then directly introduced into the vacuum container. The volume ratio of blood sample to reagent preservative is 30:1.

The resulting lysable preserved anticoagulated blood composition is gently mixed by inversion and stored at 25° C.

EXAMPLE IV

Preserved lysable anticoagulated blood compositions similar to that described in Example III are prepared wherein in lieu of dextrose, the following saccharides are used:
monosaccharides: fructose, galactose
disaccharides: sucrose, maltose
trisaccharides: raffinose

EXAMPLE V

A preserved lysable anticoagulated blood composition which can be stored at 25° C for at least 48 hours comprising a mixture of blood sample and preservative reagent, the latter consisting of an aqueous mixture of dextrose, formaldehyde, $K_3EDTA$ and sodium chloride wherein the resulting preserved blood composition contains dextrose, formaldehyde, $K_3EDTA$ and sodium chloride in amounts of 0.09% by weight, 0.6% by weight, 0.15% by weight and 0.4% by weight respectively is prepared as follows:

An aqueous mixture, in distilled or deionized form, containing 0.1% by weight of dextrose, 0.66% by weight of formaldehyde, 0.17% by weight $K_3EDTA$ and 0.45% by weight of sodium chloride is filtered through an 0.8 μ filter and combined with whole blood sample and the volume ratio of blood sample to reagent preservative is 1 to 9.

The resulting lysable preserved anticoagulated blood composition is gently mixed by inversion and stored at 25° C.

It should be understood by those skilled in the art that various modifications may be made in the present invention without departing from the spirit and scope thereof as described in the specification and defined in the appended claims.

What is claimed is:

1. A preserved lysable anticoagulated blood composition comprising a mixture of blood sample and preservative reagent wherein said preservative reagent comprises an aqueous mixture of a mono-, di- or trisaccharide component and formaldehyde, the resulting preserved blood composition containing said saccharide in the range of from 0.05% to 1.0% by weight and said formaldehyde in the range of from 0.1% to 0.8% by weight.

2. The blood composition of claim 1 wherein said saccharide component is a monosaccharide.

3. The blood composition of claim 2 wherein said monosaccharide is dextrose and the resulting preserved blood composition contains dextrose and formaldehyde in amounts of 1% by weight and 0.2% by weight respectively.

4. The blood composition of claim 2 wherein said monosaccharide is dextrose and the resulting preserved blood composition contains dextrose and formaldehyde in amounts of 0.66% by weight and 0.13% by weight respectively.

5. In a method for enhancing the preservative characteristics of whole blood samples comprising a mixture of whole blood sample and preservative reagent, the improvement which comprises adding a filtered aqueous mixture of a mono-, di- or trisaccharide component and formaldehyde to a fresh whole blood sample, the resulting preserved anticoagulated blood composition containing said saccharide in the range of from 0.05% to 1.0% by weight and said formaldehyde in the range of from 0.1% to 0.8% by weight, mixing the resulting preserved blood composition and storing same until ready for testing.

6. The method of claim 5 wherein anticoagulent is contained in the preservative reagent.

7. The method of claim 5 wherein anticoagulent is contained in the blood sample.

8. The method of claim 5 wherein said saccharide component is a monosaccharide.

9. The method of claim 8 wherein said monosaccharide is dextrose and the resulting preserved blood composition contains dextrose and formaldehyde in amounts of 1% by weight and 0.2% by weight respectively and is stored at 4° C.

10. The method of claim 8 wherein said monosaccharide is dextrose and the resulting preserved blood composition contains dextrose and formaldehyde in amounts of 0.66% by weight and 0.13% by weight respectively and is stored at 25° C.

11. The method of claim 5 wherein said aqueous mixture is filtered through an 0.8 μ filter.

12. The method of claim 5 wherein said resulting preserved blood composition is stored at a temperature in the range from 1° C to 25° C.

13. The method of claim 5 wherein said mixing step is accomplished by inversion.

* * * * *